United States Patent [19]

Ogawa

[11] Patent Number: 5,068,183

[45] Date of Patent: Nov. 26, 1991

[54] METHOD FOR MEASUREMENT OF α-AMYLASE ACTIVITY

[75] Inventor: Zensuke Ogawa, 4459-3 Fujisawa, Fujisawa-shi, Kanagawa, Japan

[73] Assignees: Kurita Water Industries, Ltd., Tokyo; Zensuke Ogawa, Fujisawa, both of Japan

[21] Appl. No.: 637,135

[22] Filed: Jan. 3, 1991

Related U.S. Application Data

[62] Division of Ser. No. 116,617, Nov. 3, 1987.

[30] Foreign Application Priority Data

Nov. 20, 1986 [JP] Japan .................................. 61-277702
Feb. 10, 1987 [JP] Japan .................................... 62-28943

[51] Int. Cl.$^5$ .......................... C12Q 1/40; C13K 1/00
[52] U.S. Cl. ....................................... 435/22; 435/202; 435/203; 435/204; 435/205; 536/103; 536/124
[58] Field of Search .................. 435/22, 202, 203, 204, 435/205; 536/103, 124

[56] References Cited

U.S. PATENT DOCUMENTS 4,081,326  3/1978  Hall ...................................... 435/274

(List continued on next page.)

FOREIGN PATENT DOCUMENTS

| 0319993 | 6/1989 | European Pat. Off. .............. 435/22 |
| 2729636 | 2/1978 | Fed. Rep. of Germany ........ 435/22 |
| 57-53079 | 11/1982 | Japan . |
| 60-172299 | 9/1985 | Japan .................................... 435/22 |
| 1-256399 | 10/1989 | Japan .................................... 435/22 |
| 2-177900 | 7/1990 | Japan .................................... 435/22 |
| 2088052 | 6/1982 | United Kingdom .................. 435/22 |

OTHER PUBLICATIONS

Marshall et al.; Clinica Chimica Acta 76:277-283 (1977).
Kobayashi et al.; Agricultural & Biological Chemistry 44(12):2991-2993 (1980).

(List continued on next page.)

*Primary Examiner*—Ronald W. Griffin
*Assistant Examiner*—Nancy S. Carson
*Attorney, Agent, or Firm*—Kanesaka and Takeuchi

[57] ABSTRACT

A for measurement of α-amylase activity uses a substrate comprising a malto-oligo saccharide represented by general formula (I) or (V) described below:

$$A - G_n - B \qquad (I)$$

$$A - G_n - I \qquad (V)$$

wherein A represents:

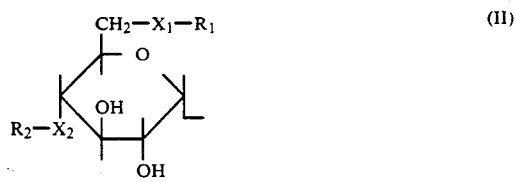

(II)

or

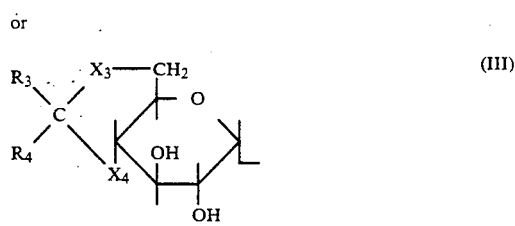

(III)

B represents a monosaccharide or a derivative thereof other than glucose; I represents inositol or a derivative thereof; G represents glucose; and n represents an integer of 3 to 15; in formula (II) or (III), $R_1$ to $R_4$ each represents a hydrogen atom, a lower alkyl group or $(CH_2)_y COOM$ (wherein y is 0, 1 or 2 and M represents a hydrogen atom or an alkali metal); and $X_1$ to $X_4$ each represents an oxygen atom or a sulfur atom. The method for measurement of α-amylase activity comprises contacting a substrate containing a malto-oligo saccharide represented by general formula (I) or (V) described above with a sample in the presence of glucosidase and measuring a liberated monosaccharide, inositol or a derivative thereof thereby to measure α-amylase activity in the sample.

8 Claims, 2 Drawing Sheets

U.S. PATENT DOCUMENTS

| | | | |
|---|---|---|---|
| 4,225,672 | 9/1980 | Hall | 435/15 |
| 4,505,756 | 3/1985 | Nix et al. | 435/22 |
| 4,794,078 | 12/1988 | Blair | 435/22 |
| 4,843,156 | 6/1989 | Miyake et al. | 536/127 |
| 4,932,871 | 6/1990 | Bell et al. | 435/22 |
| 4,945,043 | 7/1990 | Gerber | 435/22 |
| 4,990,445 | 2/1991 | Poudrier et al. | 435/22 |

OTHER PUBLICATIONS

Ferenci et al.; Biochimica et Bio-physica Acta 860:44–50 (1986).

Tokunaga et al.; Chemical Abstracts 104:74816h (1986).

Nakamura et al.; Chemical Abstracts 104:107812; (1986).

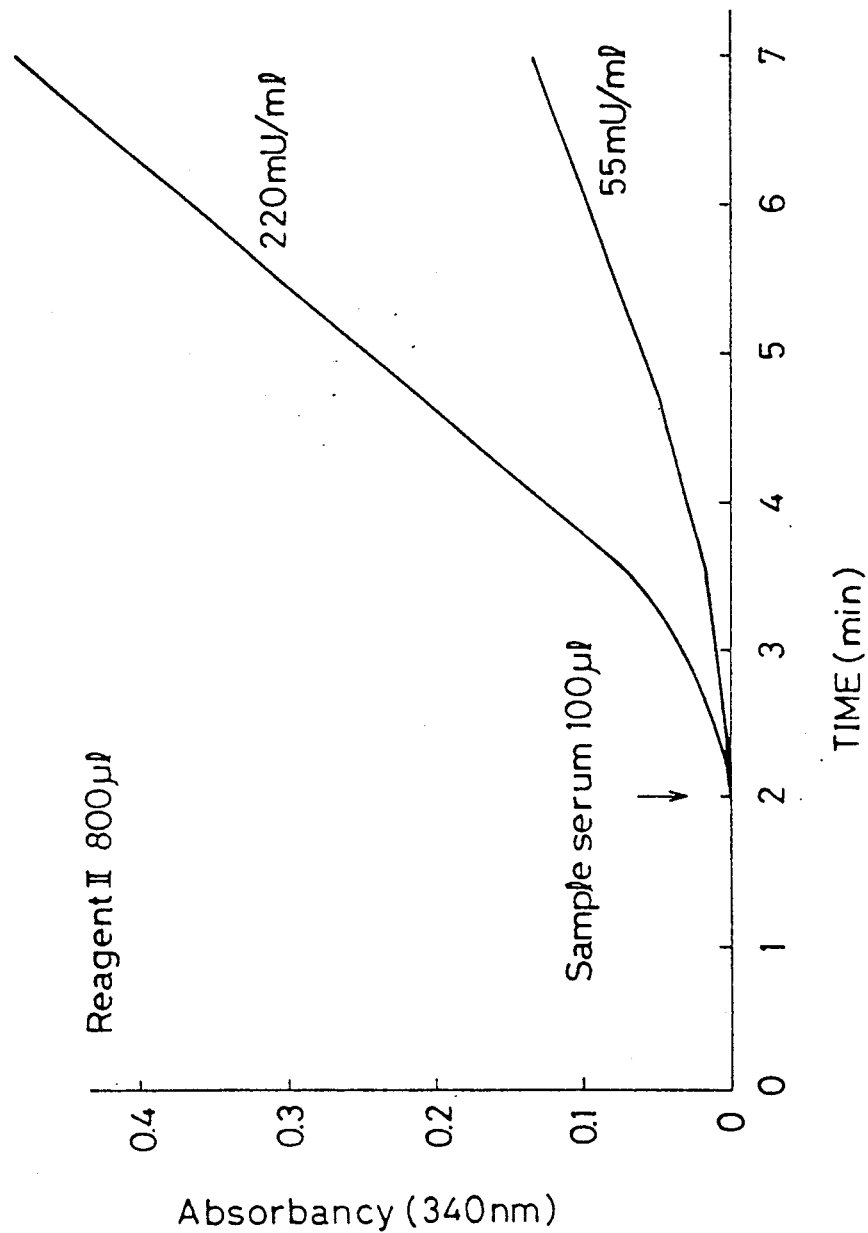

METHOD FOR MEASUREMENT OF α-AMYLASE ACTIVITY

This is a division of application Ser. No. 116,617, filed Nov. 3, 1987.

FIELD OF THE INVENTION AND RELATED ART STATEMENT

The present invention relates to a method for measurement of α-amylase activity using a substrate.

For diagnosis of acute pancreatitis, parotitis, etc. there is known a method for measuring α-amylase activity in serum or urine.

As a substrate for measurement for α-amylase activity, starch has been heretofore used but there was a difficulty in accuracy. For this reason, in recent years, malto-oligo saccharides represented by malto-pentose ($G_5$) have been adopted as substrates for measurement for α-amylase activity. That is, when α-glucosidase is used as a coupled enzyme of α-amylase, the α-amylase activity can be measured by the following method.

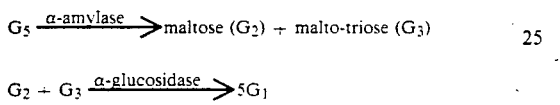

The thus produced glucose ($G_1$) is quantitatively assayed by, for example, glucose oxidase/peroxidase/-dye system or hexokinase/phosphoglucomutase/-glucose-6-phosphate dehydrogenase/NADH system or the like to measure the α-amylase activity.

Further, there has been recently proposed a method for measurement of α-amylase activity by introducing phenolic compounds such as p-nitrophenol or the like as aglycon into the reducing-end glucose, liberating aglycon and measuring its spectrum absorption (Published Examined Japanese Patent Application No. 53079/82).

In the case of using the aforesaid malto-oligo saccharide as a substrate for measurement of α-amylase activity, however, measurement error occurs because endogenous glucose or maltose in serum or urine used as a sample is present and such affect the measurement. Therefore, in the case of using malto-oligo saccharide as a substrate for measurement of α-amylase activity, it was necessary to previously treat glucose in the sample using hexokinase, etc.

On the other hand, in the case of using the phenolic compound as aglycon in the method of published Examined Japanese Patent Application No. 53079/82, the liberated chromophore is affected by various substances co-present in the sample and absorbancy tends to change and as a result, accuracy in measurement decreases in some occasion.

As such, any of conventional methods for measurement of α-amylase activity involves problems in operation, measurement accuracy, etc.

OBJECT AND SUMMARY OF THE INVENTION

An object of the present invention is to provide a method for measurement of α-amylase activity which has solved the aforesaid problems in the conventional methods, is not affected by endogeneous glucose or maltose and is capable of measuring absorbancy in high accuracy.

Another object of the present invention is to provide a method for measurement of α-amylase activity which enables to efficient measurement of α-amylase activity accurately and stably.

The features of the present invention reside in a substrate for measurement of α-amylase activity comprising a malto-oligo saccharide represented by general formula (I) or (V) described below:

wherein A represents:

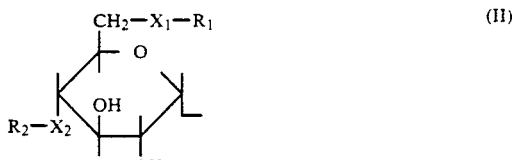

or

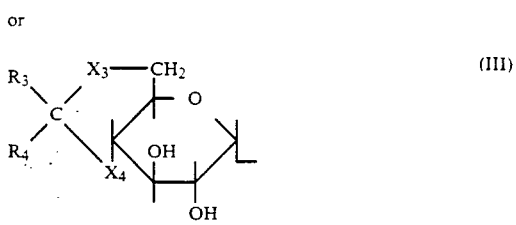

B represents a monosaccharide or a derivative thereof other than glucose; I represents inositol or a derivative thereof; G represents glucose; and n represents an integer of 3 to 15; in formula (II) or (III), $R_1$ to $R_4$ each represents a hydrogen atom, a lower alkyl group or $(CH_2)yCOOM$ (wherein y is 0, 1 or 2 and M represents a hydrogen atom or an alkali metal); and $X_1$ to $X_4$ each represents an oxygen atom or a sulfur atom.

The method for measurement of α-amylase activity comprises contacting the substrate containing a malto-oligo saccharide represented by general formula (I) or (V) described above with a sample in the presence of glucosidase and measuring a liberated monosaccharide, inositol or a derivative thereof thereby to measure α-amylase activity in the sample.

BRIEF DESCRIPTION OF THE DRAWINGS

FIG. 2 is a graph showing the results obtained by measurement of change in absorbancy obtained in Example 5.

DESCRIPTION OF THE PREFERRED EMBODIMENTS

Figure 1:
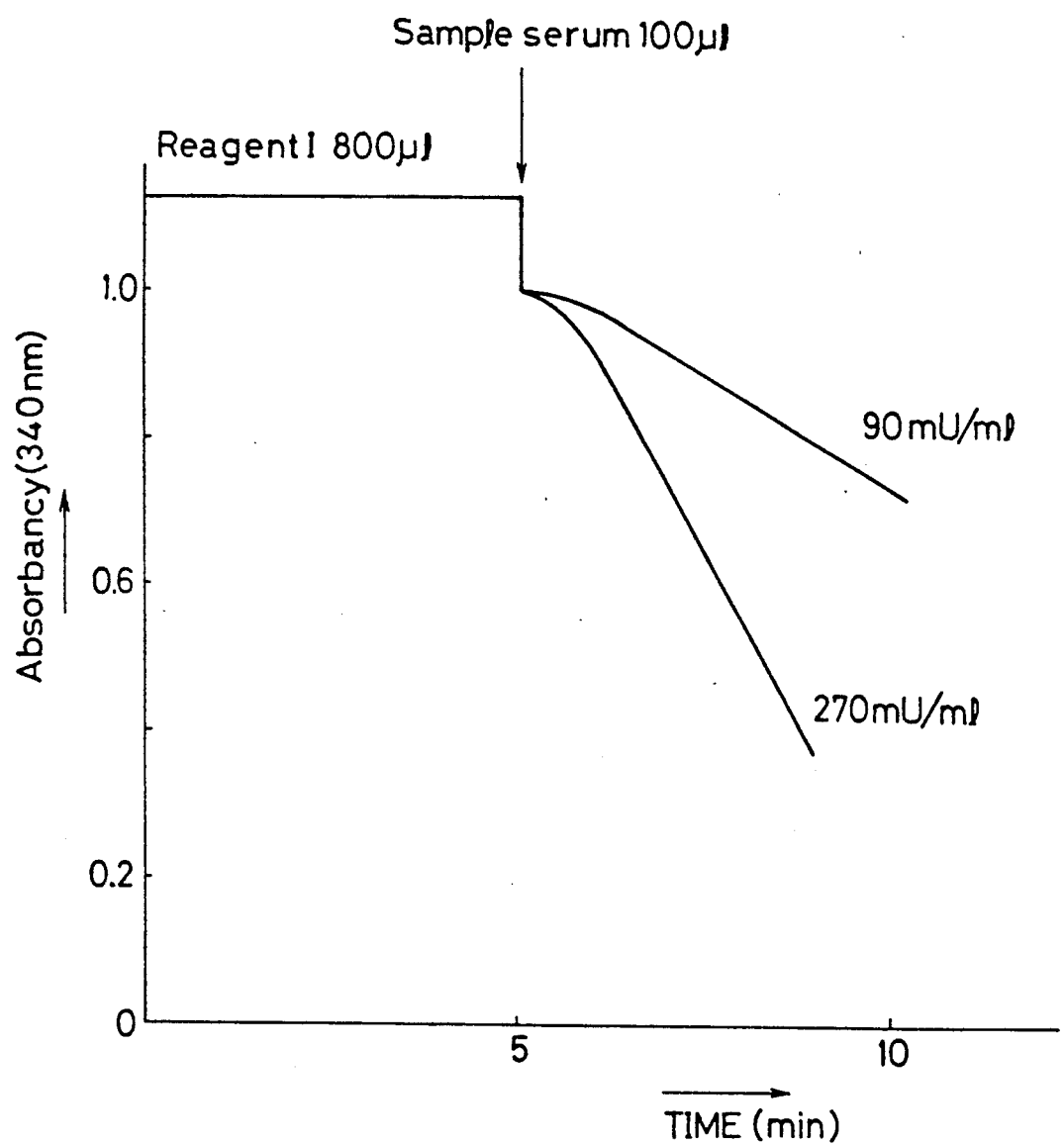
FIG. 1 is a graph showing the results obtained by measurement of change in absorbancy obtained in Example 2.

Hereafter the present invention will be described in detail.

In the substrate for measurement of α-amylase activity of the present invention, A which is the non-reducing end of the malto-oligo saccharide represented by general formula (I) or (V) may be unsubstituted glucose or may be substituted at the 4-position and/or 6-position of glucose (namely, general formula (II) described above). Further A may be one that the 4-position of glucose forms an alkylene bridge together with the 6-position (namely, general formula (III) described above).

As such, in general formula (I), A includes non-modified (unsubstituted) and modified (substituted) glucoses. Even if A is non-modified glucose, the substrate of the present invention can measure α-amylase activity much more accurately than in conventional substrates, but from the reason described below, it is preferred that A be a modified glucose.

That is, when the non-reducing end is glucose per se in substrates composed of malto-oligo saccharides, glucosidase which is a coupled enzyme used upon measurement of α-amylase activity cleaves a part of non-reducing end glucoses and makes an error in measurement of α-amylase activity in some occasion.

Examples of the modified non-reducing ends include those having introduced substituents as shown in Table 1 (a) and (b) described below in general formula (II) or (III) described above.

TABLE 1

| | (a) General Formula (II) | | | |
|---|---|---|---|---|
| No. | $X_1$ | $X_2$ | $R_1$ | $R_2$ |
| 1 | O | O | $CH_3$ | $CH_3$ |
| 2 | O | O | $CH_3$ | H |
| 3 | O | S | H | $C_2H_5$ |
| 4 | S | S | $CH_3$ | $CH_3$ |
| 5 | S | O | $CH_3$ | H |
| 6 | S | S | H | $CH_3$ |
| 7 | O | O | COOH | $CH_3$ |

| | (b) General Formula (III) | | | |
|---|---|---|---|---|
| No. | $X_3$ | $X_4$ | $R_3$ | $R_4$ |
| 8 | O | O | $CH_3$ | H |
| 9 | O | S | H | $CH_3$ |
| 10 | S | O | H | $C_2H_5$ |
| 11 | O | O | $CH_3$ | $CH_3$ |

In general formula (I), specific examples of A-Gn include malto-pentose ($G_5$), malto-octanose ($G_8$), malto-decaose ($G_{10}$) malto-hexadecaose ($G_{16}$), etc. Among them, $G_5$ to $G_8$ are preferred because they are excellent in water solubility and it is highly possible to uniformly undergo actions of 2 isoenzymes.

In general formula (I), B which becomes the reducing end represents a monosaccharide other than glucose and a derivative thereof. The reason why B does not include glucose is to distinguish B over endogenous glucose. Specific examples of B include fructose, mannose, galactose, sorbose, tagatose, etc. As the derivatives there are those having introduced a phosphate group therein. Of these, fructose is most preferred because of easy accessibility, reactivity, etc.

Among compounds represented by general formula (I), compounds represented by the following formula (IV) are most preferred as the substrates for measurement of α-amylase activity:

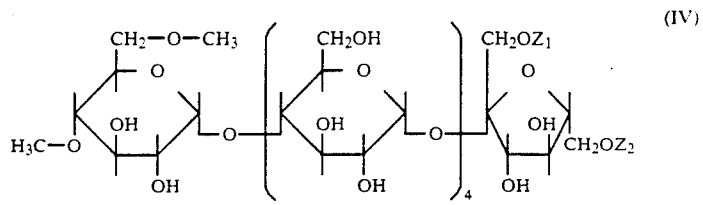

wherein $Z_1$ and $Z_2$ each represents a hydrogen atom or a phosphate group.

Hereinafter, the compounds of general formula (IV) described above are sometimes referred to as $MeG_5F$.

Further in general formula (V), I which becomes the reducing end is inositol or a derivative thereof. By using inositol as I, I can be distinguished over endogenous glucose as described above.

In the compounds represented by general formula (V), most preferred substrate for measurement of α-amylase activity are compounds represented by the following formula (VI):

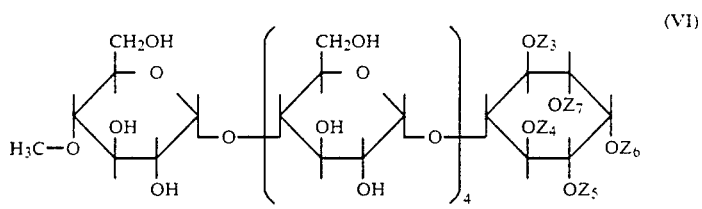

wherein $Z_3$ to $Z_7$ each represents a hydrogen atom or a phosphate group.

Hereinafter the compounds represented by general formula (VI) described above may be sometimes referred to as $G_5I$.

Next, an example of the method for producing malto-oligo saccharides represented by general formula (I) or (V) is shown.

Firstly, cyclodextrin (which may be any of α, β and γ) is reacted with monosaccharides other than glucose, for example, sucrose (G+F) (in the case of malto-oligo saccharide in general formula (I)) or inositol (in the case of malto-oligo saccharide in general formula (V)) in the presence of cyclodextrin glucanotransferase. As a result, cyclodextrin is ring-opened and, sucrose or inositol is rearranged onto the respective reducing ends and a new reducing end becomes fructose or inositol. In this case, dextrin is also cleaved so that the obtained dextrin is not limited only to the glucose number of the raw cyclodextrin but forms the glucose number lower than that. When the glucose number of malto-oligo saccharide is less than a desired number, oligosaccharides higher than maltose may be again reacted with the obtained rearranged dextrin in the presence of cyclodextrin glucanotransferase.

As has been described above, it is preferred that the non-reducing end glucose A in general formula (I) be modified at the 4-position and/or 6-position thereof, because the measurement of α-amylase activity becomes much more accurate. In the case of modifying the 4-position and/or 6-position of the non-reducing end, the monosaccharide-rearranged malto-oligo saccharide obtained by the method described above is reacted with dimethoxytoluene or methoxypropane in the presence of an acid catalyst. As a result, the non-reducing end represented by general formula (III) can be obtained.

On the other hand, in the case of introducing the non-reducing end represented by general formula (II), 6-position and/or 4-position of the compound represented by general formula (III) described above is changed to OH groups in the presence of a catalyst and an alkyl halide is then reacted therewith followed by catalytic reduction. Further in the case of converting any one of $X_1$ to $X_4$ into S, the compound represented by general formula (II) or (III) may be converted into a sulfonic acid ester followed by reacting a mercaptan with the ester.

In the example described above, it is shown that sucrose is employed as a raw material in the case of introducing fructose into the non-reducing end but maltosyl sucrose may also be used as the raw material. Further, commercially available malt-oligo saccharides may also be used in stead of cyclodextrin. As cyclodextrin glucano-transferase, those derived from Bacillus macerans, Bacillus megaterium, Bacillus circulans and Bacillus obencis, etc. as orgins thereof may be used.

As a means for isolating and purifying the desired malto-ligo saccharide from the thus obtained reaction product solution, mention may be made of GPC, ion exchange chromatography, a method using a synthetic adsorbent or the like.

Next, a method for measurement of α-amylase activity in a sample according to the method of the present invention using the malto-oligo saccharide represented by general formula (I) or (V) will be described below.

When the substrate and glucosidase as a coupled enzyme are added to a sample such as a body fluid or the like, the reaction proceeds as shown below in the case of the malto-oligo saccharide represented by general formula (I) (hereinafter $MeG_5F$ represented by general formula (IV) is used as a specific example of general formula (I)).

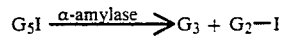

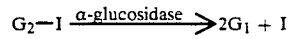

The thus liberated monosaccharides such as fructose or the like and derivatives thereof are reacted with, for example, mannitol dehydrogenase (MDH) or sorbitol dehydrogenase (SDH) in the presence of NADH thereby to produce AND; by the change in absorbancy, the amount of fructose can be determined.

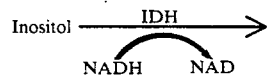

That is, the malto-oligo saccharide represented by general formula (I) is cleaved by α-amylase and glucosidase as the coupled enzyme in the sample to form monosaccharides such as fructose, etc. By quantitatively assaying the malto-oligo saccharides with, for example, MDH, SDH or the like, the α-amylase activity in the sample can be determined.

On the other hand, in the case of using the malto-oligo saccharide represented by general formula (V), when the substrate and glucosidase as a coupled enzyme are added to a sample such as a body fluid or the like, the reaction proceeds as shown below (hereinafter $G_5I$ represented by general formula (VI) is used as a specific example of general formula (V)).

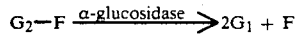

The thus liberated inositol or derivatives thereof are reacted with inositol dehydrogenase (IDH) in the presence of NAD thereby to produce NADH; by the change in absorbancy, the amount of inositol can be determined.

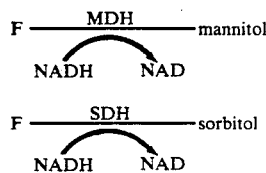

2,4,6/3,5-pentahydroxycyclohexanone

As such, the substrate represented by general formula (V) used in the present invention is cleaved by α-amylase and glucosidase as the coupled enzyme in the sample to produce inositol or derivatives thereof. By dehydrogenating the inositols with, for example, IDH or the like, a color forming reaction of NAD→NADH, whereby the produced NADH amount is measured to determine the α-amylase activity.

The method of measurement in accordance with the present invention utilizes a color change reaction of NAD⇌NADH, and the measurement can be made in high sensitivity with high accuracy.

As described above in detail, the substrate for measurement of α-amylase activity contains the malto-oligo saccharide represented by general formula (I) or (V). The malto-oligo saccharide is cleaved by α-amylase and the coupled enzyme glucosidase in the sample to prouce monosaccharides or inositol, whereby quantitative assay is enabled. In this case, the monosaccharide other than glucose or inositol is rearranged at the reducing end of saccharide so that there is no chance of being affected by endogenous glucose, maltose or the like contained in a sample. Accordingly, by the use of the substrate for measurement of α-amylase activity of the present invention, α-amylase activity can be measured accurately and efficiently. Further by introducing modified glucose in the non-reducing end of general formula (I), accuracy of the measurement can be more improved.

Further in the method for measurement of α-amylase activity, the malto-oligo saccharide represented by general formula (I) or (V) is contacted with a sample in the presence of glucosidase and the thus liberated monosaccharide or inositol or derivatives thereof is measured thereby to determine α-amylase activity in the sample, whereby α-amylase activity can be measured stably with high accuracy. In particular, by treating the liberated monosaccharide with an enzyme in the presence of NAD or NADH, NAD or NADH can be obtained; in this case, the measurement of absorbancy can be made stably without being affected by other contaminants in the sample. Further by treating inositol with an enzyme in the presence of NAD, NADH can be obtained; in this case, the measurement of absorbancy can be made stably without being affected by other contaminants in the sample.

Hereafter the present invention will be described in more detail with reference to the examples below.

EXAMPLE 1

Production of MeG$_5$F

To 29.5 g of commercially available G$_5$ were added 140 ml of pyridine and 140 ml of acetic anhydride. The mixture was reacted at room temperature to give 51.8 g of peracetated G$_5$. In 165 ml of chloroform was dissolved 25.0 g of the obtained peracetated G$_5$. The solution was reacted with 30% HBr-acetic acid at 10° C. or below for 2 hours to give 24.5 g of peracetated G$_5$ bromide The peracetated G$_5$ bromide was reduced with 6.7 g of Hg(CN)$_2$ and 33 ml of benzyl alcohol in benzene for 2 hours to give peracetated G$_5$ benzyl glycoside. Then peracetated G$_5$ benzyl glycoside was hydrolyzed with sodium methoxide in methanol at room temperature to give 19.9 g of benzyl glycosidated G$_5$.

By reacting 19.9 g of benzyl glycosidated G$_5$ with 14.8 g of benzaldehyde dimethyl acetal in DMF in the presence of p-toluenesulfonic acid catalyst at 85°-90° C. for 4 hours, non-reducing end-4,6-0-benzylidene benzyl glycosidated G$_5$ was obtained.

The non-reducing end-4,6-0-benzylidene benzyl glycosidated G$_5$ was reacted with 100 ml of pyridine and 100 ml of acetic anhydride at room temperature for 48 hours to give 26.2 g of non-reducing end-4,6-O-benzylidene benzyl glycosidated G$_5$ peracetate. By reacting 26.2 g of non-reducing end-4,6-O-benzylidene benzyl glycosidated G$_5$ peracetate with 180 ml of benzyl chloride in 370 ml of dioxan together with 180 g of KOH at 105° to 110° C. for 6 hours, non-reducing end-4,6-O-benzylidene perbenzylated G$_5$ was obtained. Further the non-reducing end-4,6-O-benzylidene perbenzylated G$_5$ was refluxed in 750 ml of acetone and 160 ml of 1N-NCl on a hot bath to split the benzylidene off, whereby 7.6 g of non-reducing end-4,6-OH-perbenzylated G$_5$, was obtained.

Under shielding from light, 84 ml of methyl iodide was reacted with 7.6 g of non-reducing end-4,6-OH perbenzylated G$_5$ in 240 ml of DMF together with 23.1 g of BaO and 9.4 g of Ba(OH)$_2$·8H$_2$O for 48 hours at room temperature to give non-reducing end-4,6-0-methyl perbenzylated G$_5$. By catalytic reduction of the non-reducing end-4,6-O-methyl perbenzylated G$_5$ with Pd in methanol/ethyl acetate at room temperature under normal pressure, 1.2 g of non-reducing end-4,6-di-O-methylated G$_5$ was obtained.

Next, this non-reducing end-4,6-di-O-methylated G$_5$ was made 10% w/v solution and an equimolar amount of 4% w/v sucrose solution was mixed therewith. Bacillus obencis-origined cyclodextrin glucanotransferase was added to the mixture followed by settling and reacting under conditions of 37° C. and pH of 6.0 for 16 hours. The reaction solution was purified by column chromatography 16 hours after to give 0.12 g of MeG$_5$F (wherein Z$_1$ and Z$_2$ are hydrogen atoms).

EXAMPLE 2

Measurement of α-amylase activity

| Reagent I was prepared by the following formulation. | |
|---|---|
| Reagent I | |
| Substrate obtained in Example 1 | 1 mmol/l (final concentration) |
| α-Glucosidase | 25 U/ml (final concentration) |
| Mannitol dehydrogenase | 40 U/ml (final concentration) |
| NADH | 0.16 mmol/l (final concentration) |
| PIPES buffer (pH 7.0) | 100 mmol/l (final concentration) |

100 mmol/1 (final concentration) To 800 μl of Reagent I described above was added 100 μl of a sample serum containing 90 mU/ml and 270 mU/ml, respectively. While incubating at 37° C. for 10 minutes, change in absorbancy was measured at 340 nm.

The results are shown in FIG. 1.

From FIG. 1, it is understood that according to the method of the present invention, a good linear relationship was obtained in any concentration after 6 minutes so that according to the present invention, α-amylase activity can be measured stably with high accuracy.

EXAMPLE 3

Measurement was performed in a similar manner except that 100 mg/ml of glucose was further added to each sample serum.

As a result, almost the same results as in FIG. 1 were obtained.

From the foregoing, it is understood that the method for measurement of α-amylase activity using the maltooligo saccharide represented by general formula (I) is not affected by endogenous glucose or the like at all.

EXAMPLE 4

Production of G$_5$I

After 200 U/g-Substrate of Bacillus obencis-origined cyclodextrin glucanotransferase was added to a solution of 20 g of β-cyclodextrin and 20 g of inositol, the mixture was reacted under conditions of 60° C. and pH of 6.0 for 25 hours. The reaction solution was subjected to separation by chromatography using a silica-packed column to give 8.8 g of G$_2$I.

Next 8 of this G$_2$I and 12 of commercially available G$_4$ oligosaccharide were dissolved in 400 ml of buffer (pH, 6.0) and, 200 U/g-Substrate of cyclodextrin glucanotransferase substrate was added to the solution followed by reacting at 37° C. for 20 minutes. Then, the reaction mixture was again subjected to separation by chromatography to give 1.8 g of G$_5$I.

EXAMPLE 5

Measurement of α-amylase activity

Reagent II was prepared by the following formulation.

| Reagent II was prepared by the following formulation. | |
|---|---|
| Reagent II | |
| Substrate obtained in Example 4 | 1 mmol/l (final concentration) |
| α-Glucosidase | 25 U/ml (final concentration) |
| Inositol dehydrogenase | 40 U/ml (final concentration |
| NAD | 40 mmol/l (final concentration) |

-continued

| Reagent II was prepared by the following formulation. | |
|---|---|
| Reagent II | |
| PIPES buffer (pH 7.0) | 100 mmol/l (final concentration) |

To 800 μl of Reagent II described above was added 100 μl of a sample serum containing 55 mU/ml and 220 mU/ml, respectively. While incubating at 37° C. for 10 minutes, change in absorbancy was measured at 340 nm.

The results are shown in FIG. 2.

From FIG. 2, it is understood that according to the method of the present invention, a good linear relationship was obtained in any concentration after 4 minutes so that according to the present invention, α-amylase activity can be measured stably with high accuracy.

EXAMPLE 6

Measurement was performed in a similar manner as in Example 5 except that 100 mg/ml of glucose was further added to each sample serum.

As a result, almost the same results as in FIG. 2 were obtained.

From the foregoing, it is understood that the method for measurement of α-amylase activity using the malto-oligo succharide represented by general formula (V) is not affected by endogeneous glucose or the like at all.

While the invention has been described in detail and with reference to specific embodiments thereof, it will be apparent to one skilled in the art that various changes and modifications can be made therein without departing from the spirit and scope thereof.

What is claimed is:

1. A method for measurement of α-amylase activity in a sample, comprising contacting a substrate containing a malto-oligo saccharide represented by general formula (I) described below with the sample in the presence of glucosidase and measuring a liberated monosaccharide or a derivative represented by B of the general formula (I) and liberated through activity of α-amylase thereby to measure α-amylase activity in the sample:

A - Gn - B  (I)

wherein A represents:

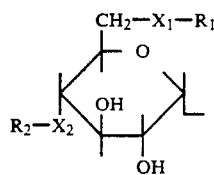

(II)

or

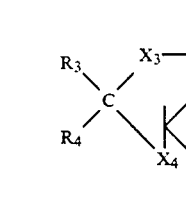

(III)

B represents a monosaccharide or a derivative thereof other than glucose; G represents glucose; and n represents an integer of 3 to 15; in formula (II) or (III), $R_1$ to $R_4$ each represents a hydrogen atom, a lower alkyl group or $(CH_2)yCOOM$ (wherein y is 0, 1 or 2 and M represents a hydrogen atom or an alkali metal); and $X_1$ to $X_4$ each represents an oxygen atom or a sulfur atom.

2. A method as claimed in claim 1 wherein B in said formula (I) is fructose.

3. A method as claimed in claim 1 wherein said malto-oligo saccharide is represented by formula (IV) described below:

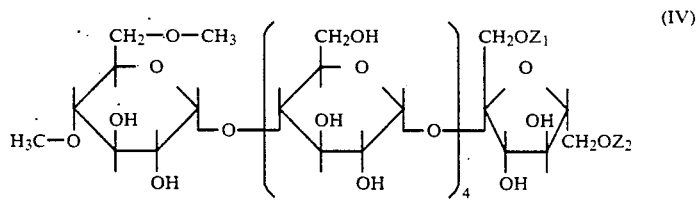

(IV)

wherein $Z_1$ and $Z_2$ each represents a hydrogen atom or a phosphate group.

4. A method as claimed in claim 1 wherein said liberated monosaccharide or a derivative thereof is reacted with mannitol dehydrogenase or sorbitol dehydrogenase in the presence of NADH to produce NAD and based on change of absorbency which is changed in accordance with the produced NAD, an amount of said liberated monosaccharide or a derivative thereof is determined.

5. A method for measurement of α-amylase activity in a sample, comprising contacting a substrate containing a malto-oligo saccharide represented by general formula (V) described below with the sample and measuring a liberated inositol or a derivative represented by I of the general formula (V) and liberated by α-amylase activity to determine α-amylase activity in the sample:

A - Gn - I  (V)

wherein A represents:

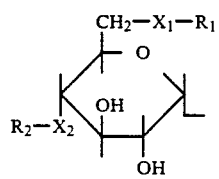

(II)

or

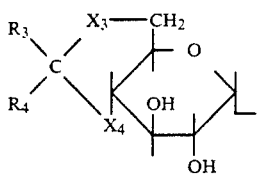

(III)

I represents inositol or a derivative thereof; G represents glucose; and n represents an integer of 3 to 15; in formula (II) or (III), $R_1$ to $R_4$ each represents a hydrogen atom, a lower alkyl group or $(CH_2)yCOOM$ (wherein Y is 0, 1 or 2 and M represents a hydrogen atom or an alkali metal); and $X_1$ to $X_4$ each represents an oxygen atom or a sulfur atom.

6. A method as claimed in claim 5 wherein I in said formula (V) is inositol.

7. A method as claimed in claim 5 wherein said malto-oligo saccharide is represented by formula (VI) described below:

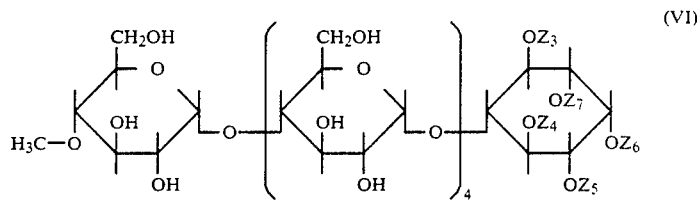

wherein $Z_3$ to $Z_7$ each represents a hydrogen atom or a phosphate group.

8. A method as claimed in claim 5 wherein said liberated inositol or a derivative thereof is reacted with inositol dehydrogenase in the presence of NAD (nicotinic amide adenine dinucleotide) and based on change of absorbancy which is changed in accordance with the produced NAD, an amount of said liberated inositol or a derivative thereof is determined.

* * * * *